US011439149B2

(12) United States Patent
Caldwell et al.

(10) Patent No.: US 11,439,149 B2
(45) Date of Patent: Sep. 13, 2022

(54) FORMULATIONS AND METHODS FOR CONTROLLING ROOTWORM LARVAE

(71) Applicant: FMC Corporation, Philadelphia, PA (US)

(72) Inventors: Nathan D. Caldwell, Morrisville, PA (US); Thomas E. Anderson, Clayton, NC (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 15/480,482

(22) Filed: Apr. 6, 2017

(65) Prior Publication Data

US 2017/0347659 A1 Dec. 7, 2017

Related U.S. Application Data

(60) Provisional application No. 62/318,997, filed on Apr. 6, 2016.

(51) Int. Cl.
*A01N 53/00* (2006.01)
*A01N 43/56* (2006.01)
*A01N 43/713* (2006.01)
*A01N 41/10* (2006.01)
*A01N 25/04* (2006.01)
*C07D 401/14* (2006.01)
*C07D 401/04* (2006.01)

(52) U.S. Cl.
CPC ............. *A01N 53/00* (2013.01); *A01N 25/04* (2013.01); *A01N 41/10* (2013.01); *A01N 43/56* (2013.01); *A01N 43/713* (2013.01); *C07D 401/04* (2013.01); *C07D 401/14* (2013.01)

(58) Field of Classification Search
CPC ....... A01N 53/00; A01N 43/56; A01N 43/713
See application file for complete search history.

(56) References Cited

U.S. PATENT DOCUMENTS

| 9,017,734 B2 | 4/2015 | Shah |
| 2013/0302446 A1* | 11/2013 | Shah |
| 2014/0329676 A1* | 11/2014 | Fischer .................. A01N 43/56 504/100 |
| 2015/0099627 A1 | 4/2015 | Martin et al. |
| 2018/0049435 A1* | 2/2018 | Sikuljak ................. A01N 37/46 |
| 2018/0139960 A1* | 5/2018 | Sikuljak ................. A01N 37/22 |

FOREIGN PATENT DOCUMENTS

| CN | 105360133 A | 3/2016 |
| WO | 20060060551 | 6/2006 |
| WO | 20130092519 | 6/2013 |
| WO | 20150055757 | 4/2015 |
| WO | 2015/189080 A1 | 12/2015 |

OTHER PUBLICATIONS

PCT/US17/26241 International Search Report dated Jun. 27, 2017.
Weinzierl, et al, "Evaluation of Attribute II Bt Sweet Corn Resistance and Reduced-Risk Insecticide Applications for Control of Corn Earworm", World Academy of Science, Engineering and Technology, International Journal of Biological, Biomolecular, Agricultural, Food and Biotechnological Engineering, vol. 8, No. 1, pp. 25-27, 2014.
Huseth, et al, "Evaluation of diamide insecticides co-applied with other agrochemicals at various times to manage Ostrinia nubilalis in processing snap bean", Pest Management Science, vol. 71, No. 12, Jan. 13, 2015, pp. 6-7.

* cited by examiner

*Primary Examiner* — Michael B. Pallay
(74) *Attorney, Agent, or Firm* — FMC Corporation (57) ABSTRACT

Tetraniliprole containing formulations and methods for using them for controlling rootworm infestation are discussed. The formulations of the present invention provide improved delivery active ingredients by the ability to provide substantially higher degree of control as compared to other diamide counterparts.

7 Claims, 4 Drawing Sheets

FORMULATIONS AND METHODS FOR CONTROLLING ROOTWORM LARVAE

FIELD OF THE INVENTION

The present invention relates to the field of agrochemical compositions and formulations. In particular, the invention provides a composition comprising a tetraniliprole alone or in combination with other plant protection agents suitable for controlling rootworm larvae in soil.

BACKGROUND OF THE INVENTION

Insects and plant pests cause millions of dollars worth of damages annually on agricultural products. Rootworms are one of the major agricultural pest insects contributing to the damages to agricultural products. These pests have a wide range of host plants and in their larval form make tunnels through the roots of young plants, stunting or killing them. They are typically native to the soil and will readily infest a field of crop plants, most notoriously corn. These pests include but are not limited to such species as *Diabrotica virgifera virgifera* (*D. virgifera*), *D. undecimpunctata undecimpunctata* (*D. undecimpunctata*), *D. barberi*, *D. u. howardi*, and *D. u. tenella*. Some are perennial pests of corn across most of the Corn Belt. Despite ongoing new pesticides and insecticides, resistance continues to emerge among such pests as *D. virgifera*, *D. undecimpunctata*, *D. barberi*, *D. u. howardi*, and *D. u. tenella*. Thus, there is a need for new techniques and compositions to combat such species of pests.

SUMMARY OF THE INVENTION

One aspect of the present invention provides compositions that exhibit enhanced activity against rootworms in their larval form. Another aspect of the present invention provides novel methods for controlling rootworms.

In one embodiment, the compositions of the present invention contain an effective amount of a diamide insecticide as the sole active ingredient. In this embodiment, the diamide insecticide includes but is not limited to tetraniliprole, chlorantraniliprole, flubendiamide, and cyantraniliprole. In certain embodiments, the diamide insecticide is tetraniliprole.

In another embodiment, the composition may further contain a plant protection agent selected from the group consisting of pesticide, arthropodicide, insecticide, acaricide, nematocide, fungicide, herbicide, plant growth regulator and a combination thereof. In a preferred embodiment, the pesticide is a pyrethroid selected from bifenthrin, cypermethrin, beta-cypermethrin, zeta-cypermethrin, deltamethrin, cis-permethrin, gamma-cyhalothrin, tralomethrin, cyfluthrin, beta-cyfluthrin, esfenvalerate and fluvalinate.

In another embodiment of the present invention, methods of controlling, stunting or killing rootworms at all stages of their life cycle in a region susceptible to their growth are described. In one embodiment, the methods are directed to controlling these pests at their larval ($1^{st}$ instar, $2^{nd}$ instar, $3^{rd}$ instar, $4^{th}$ instar), pupal, and adult stages. In a preferred embodiment, the rootworms include but are not limited to such species as *D. virgifera*, *D. barberi*, *D. u. howardi*, *D. u. tenella*, and *D. undecimpunctata*.

In another embodiment, the composition of the present invention is present in the liquid form of a microemulsion, an oil-in-water concentrated emulsion, a suspension, a suspension concentrate, an emulsifiable concentrate, or a microencapsulate. In at least one embodiment, the composition of the present invention is in the form of a suspension concentrate (SC). In yet another embodiment, the suspension concentrate is stable over a time period of two years or more wherein the suspended particles do not aggromelate. In yet another embodiment, the diamide compound is tetraniliprole as a 200 SC formulation (Test Formula).

In an alternate embodiment, the composition of the present invention is a combination of the diamide insecticide and a plant protecting agent such as a pyrethorid. In one embodiment, the diamide insecticide is tetraniliprole and the plant protecting agent is bifenthrin.

In another embodiment, the composition may further contain a dispersant, a preservative, a foaming agent, and/or at least one foam stabilizer. In another embodiment, the composition may be applied in a furrow in the form of foam. In certain embodiments, the foaming agent can be sodium lauryl sulfate, sodium dodecylbenzene sulfonate, or a combination thereof. In another embodiment, the foam stabilizer can be glycerine, xanthan gum, or a combination thereof. In yet another embodiment, the foam may have an expansion factor of 15, 25, 40, 50, 60 or 70.

In another embodiment, the compositions of the present invention may be mixed into water and/or liquid fertilizer and applied in-furrow at a volume of 10, 9, 8, 7, 6, 5, 4, 3, 2 gallons or less per acre.

In another embodiment, tetraniliprole and a plant protection agent may be applied each at a rate ranging from about 0.05 lb ai/acre to about 10 lb ai/acre, all sub-ranges and sub-values included. In exemplary embodiments, tetraniliprole and the plant protection agent may be applied independently at a rate of about 0.05, about 0.1, about 0.15, about 0.2, about 0.25, about 0.3, about 0.35, about 0.4, about 0.45, about 0.5, about 0.6, about 0.7, about 0.8, about 0.9, about 1.0, about 1.2, about 1.4, about 1.6, about 1.8, about 2.0, about 2.5, about 3, about 3.5, about 4, about 4.5, about 5, about 6, about 7, about 8, about 9, or about 10 lb/acre.

In another embodiment, the formulation can be applied to the soil or to the plant as a rescue treatment or post-plant to control rootworm larvae.

Another objective of the present invention is to reduce the application rates and broaden the activity spectrum of the compositions claimed herein by reducing the total amount of active compounds applied. In another embodiment, It is an objective of the present invention to provide a composition which, when applied to a crop, results in a decreased amount of residues in the crop, thereby reducing the risk of resistance formation and nevertheless providing efficient plant disease control.

BRIEF DESCRIPTION OF THE DRAWINGS

A detailed description of drawings is provided here to illustrate various aspects and features of the present subject matter.

FIGS. 1-A to 1-G provides schematic representation of methodology steps for assessing rootworms within treated soil. (FIG. 1-A) pre-water submerged corn seeds are placed between layers of moisten paper towel. (FIG. 1-B) Test Formulation according to the present invention was mixed with the soil. (FIGS. 1-C and 1-D) treated soil was placed in the container along with two germinated corn seeds on top. (FIGS. 1-E and 1-F) 5 larvae of Southern Corn Root Worms (SCRW) and Western Corn Root Worms (WCRW) were placed onto the soil in a container and capped (FIG. 1-G) arenas containing soil, corn, and larvae to be evaluated.

FIGS. 2-A and 2-B shows WCRW larvae extracted from the untreated soil after 6 d (FIG. 2-A) and the soil treated with the Test Formulation 57 days after the treatment (FIG. 2-B) (designated as number 8) at 67 ppm and pH of 8.

FIGS. 3-A to 3-C depicts the corn plants extracted from a soil that has been treated with Test Formulation at 15 g ai/ha (FIG. 3-A), Capture LFR at 112 g ai/ha (FIG. 3-B), or the soil that was untreated (FIG. 3-C). The extraction occurred 5 days after being within the subject soils. The respective soils were infested with 5, 2nd instar WCRW larvae.

FIGS. 4-A to 4-B depicts the damage to corn roots and shoots caused by 2nd instar WCRW infested into the respective treated soil. (FIG. 4-A) depicts the damage to the crop in soil treated with Test Formulation at 60 g ai/ha=1069 ppm. (FIG. 4-B) depicts the damage to the crop in an untreated soil. The assessment was done at 144 hour post WCRW infestation.

DETAILED DESCRIPTION OF THE INVENTION

Various embodiments of the present invention provide an agricultural composition for controlling rootworms. At least one aspect of the present invention is directed to the novel discovery of compositions containing diamide compounds that exhibit potent activities in controlling and suppressing rootworm pests, particularly in their larval form. Even more surprising and unexpected is the activity spectrum of tetraniliprole against these pests.

As used in this specification and unless otherwise indicated, the term "rootworms" includes but is not limited to *D. virgifera* (also known and refereed herein as Western corn rootworm "WCRW"), *D. barberi* (also known and referred herein as Northern corn rootworm "NCR"), *D. u. howardi*, *D. u. tenella*, and *D. undecimpunctata* (also known and referred herein as Southern corn rootworm "SCRW").

As used in this specification and unless otherwise indicated the term "plant protection agent" refers to a molecule or combination of molecules which express biological activity as a pesticide, arthropodicide, insecticide, acaricide, nematocide, fungicide, herbicide, plant growth regulator or a combination of two or more of these biological activities.

As used in this specification and unless otherwise indicated, the term "controlling" refers to reducing, inhibiting, or eliminating the presence of rootworm species during one or more of its growth stages. For example, the compositions of the present invention may be used for controlling the growth of rootworms at any instar stages as well as its pupil and adult forms.

As used in this specification and unless otherwise indicated, the term "insecticide" refers to a molecule or combination of molecules that repels, retards, or kills insects, and can be used for plant protection, edifice protection, turf protection, or protection of a person.

The term "liquid fertilizer" refers to a fertilizer in a fluid or liquid form containing various ratios of nitrogen, phosphorous and potassium (for example, but not limited to, 10% nitrogen, 34% phosphorous and 0% potassium) and micronutrients, commonly known as starter fertilizers that are high in phosphorus and promote rapid and vigorous root growth. Liquid fertilizers are commonly aqueous-based. As used herein, the term "aqueous-based" indicates that the predominant solvent or vehicle is water. The term "ambient temperature" as utilized herein shall mean any suitable temperature found in a laboratory or other working environment, and is generally not below about 15° C. nor above about 30° C.

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a concentration of about 200 grams per liter in reference to, for example, a formulation would be interpreted to include other like concentrations that can be expected to provide similar effect for the concentration, such as 180 grams per liter or 220 grams per liter. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

In one aspect of the present invention, novel compositions are described for controlling rootworms that contain at least one diamide compound selected from the group consisting of flubendiamide, chloranthraniliprole, cyanthraniliprole and tetraniliprole in a carrier system in amounts effective to inhibit the infestation of the larvae in a location of interest. In at least another aspect of the invention, combinations of a diamide compound with one or more plant protection agents are described to broaden the spectrum for insecticidal efficacy.

In another aspect of the present invention, methods for controlling infestation of *Diabrotica* larvae in a location of interest are described. In at least one embodiment, the controlling of larvae results in at least 60, 70, 80, 90 or 100% inhibition of larvae in such location. According to certain embodiments, methods of controlling infestation *Diabrotica* larvae at all its life stages can be achieved by applying a composition comprising a diamide compound selected from the group consisting of flubendiamide, chloranthraniliprole, cyanthraniliprole or tetraniliprole and a carrier system in amounts effective to inhibit the infestation of the larvae in a location of interest. In another embodiment, the diamide compound is tetraniliprole.

In another embodiment a method for controlling infestation of *Diabrotica* larvae in a location is described comprising (a) applying an amount of a composition comprising a liquid agricultural formulation comprising an active ingredient selected from the group consisting of flubendiamide, chloranthraniliprole, cyanthraniliprole and tetraniliprole and an agriculturally suitable carrier system in amounts effective and optionally a plant protecting agent, and (b) inducing mortality in at least 60% of said larvae. In one embodiment, the larve mortality rate is in at least 70%, 80%, 90%, 95%, 98%, or 99% in such locations. In at least one embodiment, the location of interest is on the plant itself, plant seed, plant roots, plant part, foliage, seedling or substrate for growing the plant or crop. In another embodiment, the larvae is NCR, WCRW, SCRW, or a combination thereof.

In at least another embodiment, the methods according to the present invention provide greater control at all instar stages of rootworm larvae as compared to other diamide insecticides such as chloranthraniliprole flubendiamide, and cyantraniliprole at a comparable rate of administration to the soil or the area of interest. In at least one embodiment, a tetraniliprole containing composition according to the the present invention unexpectedly provides a statistically greater control of SCRW and WCRW as compared to cyantraniliprole and chloranthranilipole. In another embodiment, the tetraniliprole containing compositions of the present invention are administered at ranges between 2.5 to 100 g ai/ha, or 7.5 to 60 g ai/ha to provide a larval mortality rate of at least 60%, 70%, 80%, 90%, 95%, 98%, or 99% in administered locations.

In another aspect of the present invention, the compositions according to the present invention consist essentially of tetraniliprole or a derivative thereof. In another embodiment, the composition contains solely a single diamide insecticide. In certain embodiments, the diamide insecticide is tetraniliprole.

In another embodiment, the compositions of the present invention further include a plant protecting agent. Suitable plant protecting agents include the following:

Insecticides: A1) the class of carbamates consisting of aldicarb, alanycarb, benfuracarb, carbaryl, carbofuran, carbosulfan, methiocarb, methomyl, oxamyl, pirimicarb, propoxur and thiodicarb; A2) the class of organophosphates consisting of acephate, azinphos-ethyl, azinphos-methyl, chlorfenvinphos, chlorpyrifos, chlorpyrifos-methyl, demeton-S-methyl, diazinon, dichlorvos/DDVP, dicrotophos, dimethoate, disulfoton, ethion, fenitrothion, fenthion, isoxathion, malathion, methamidaphos, methidathion, mevinphos, monocrotophos, oxymethoate, oxydemetonmethyl, parathion, parathion-methyl, phenthoate, phorate, phosalone, phosmet, phosphamidon, pirimiphos-methyl, quinalphos, terbufos, tetrachlorvinphos, triazophos and trichlorfon; A3) the class of cyclodiene organochlorine compounds such as endosulfan; A4) the class of fiproles consisting of ethiprole, fipronil, pyrafluprole and pyriprole; A5) the class of neonicotinoids consisting of acetamiprid, chlothianidin, dinotefuran, imidacloprid, nitenpyrathiacloprid and thiamethoxam; A6) the class of spinosyns such as spinosad and spinetoram; A7) chloride channel activators from the class of mectins consisting of abamectin, emamectin benzoate, ivermectin, lepimectin and milbemectin; A8) juvenile hormone mimics such as hydroprene, kinoprene, methoprene, fenoxycarb and pyriproxyfen; A9) selective homopteran feeding blockers such as pymetrozine, flonicamid and pyrifluquinazon; A10) mite growth inhibitors such as clofentezine, hexythiazox and etoxazole; A11) inhibitors of mitochondrial ATP synthase such as diafenthiuron, fenbutatin oxide and propargite; uncouplers of oxidative phosphorylation such as chlorfenapyr; A12) nicotinic acetylcholine receptor channel blockers such as bensultap, cartap hydrochloride, thiocyclam and thiosultap sodium; A13) inhibitors of the chitin biosynthesis type 0 from the benzoylurea class consisting of bistrifluron, diflubenzuron, flufenoxuron, hexaflumuron, lufenuron, novaluron and teflubenzuron; A14) inhibitors of the chitin biosynthesis type 1 such as buprofezin; A15) moulting disruptors such as cyromazine; A16) ecdyson receptor agonists such as methoxyfenozide, tebufenozide, halofenozide and chromafenozide; A17) octopamin receptor agonists such as amitraz; A18) mitochondrial complex electron transport inhibitors pyridaben, tebufenpyrad, tolfenpyrad, flufenerim, cyenopyrafen, cyflumetofen, hydramethylnon, acequinocyl or fluacrypyrim; A19) voltage-dependent sodium channel blockers such as indoxacarb and metaflumizone; A20) inhibitors of the lipid synthesis such as spirodiclofen, spiromesifen and spirotetramat; A21) ryanodine receptor-modulators from the class of diamides consisting of flubendiamide, the phthalamide compounds (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and (S)-3-Chlor-N1-{2-methyl-441,2,2,2-tetrafluor-1-(trifluormethyl)ethyl]phenyl}-N2-(1-methyl-2-methylsulfonylethyl)phthalamid, chloranthraniliprole, and cyanthraniliprole; A22) compounds of unknown or uncertain mode of action such as azadirachtin, amidoflumet, bifenazate, fluensulfone, piperonyl butoxide, pyridalyl, sulfoxaflor; or A23) sodium channel modulators from the class of pyrethroids consisting of acrinathrin, allethrin, bifenthrin, cyfluthrin, lambda-cyhalothrin, cyper-methrin, alpha-cypermethrin, beta-cypermethrin, zeta-cypermethrin, deltamethrin, esfenvalerate, etofenprox, fenpropathrin, fenvalerate, flucythrinate, taufluvalinate, permethrin, silafluofen and tralomethrin.

Fungicides: B1) azoles selected from the group consisting of bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thia-bendazole, fuberidazole, ethaboxam, etridiazole and hymexazole, azaconazole, diniconazole-M, oxpoconazol, paclobutrazol, uniconazol, 1-(4-chloro-phenyl)-2-([1,2,4]triazol-1-yl)-cycloheptanol and imazalilsulfphate; B2) strobilurins selected from the group consisting of azoxystrobin, dimoxystrobin, enestroburin, fluoxastrobin, kresoximmethyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-yl-methoxyimino)ethyl]benzyl)carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxyphenyl)-cyclopropanecarboximidoylsulfanylmethyl)-phenyl)-acrylic acid methyl ester; B3) carboxamides selected from the group consisting of carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(443-(4-chlorophenyl)prop-2-ynyloxyl-3-methoxyphenyl)ethyl)-2-methanesulfonyl-amino-3-methylbutyramide, N-(2-(4-[3-(4-chloro-phenyl)prop-2-ynyloxy]-3-methoxy-phenyl)ethyl)-2-ethanesulfonylamino-3-methylbutyramide, methyl 3-(4-chlorophenyl)-3-(2-isopropoxycarbonyl-amino-3-methyl-butyrylamino) propionate, N-(4'-bromobiphenyl-2-yl)-4-difluoromethylA-methylthiazole-6-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3 \4'-dichloro-4-fluorobiphenyl-2-yl)-3-difluoro-methyl-1-methyl-pyrazole-4-carboxamide, N-(3',4'-dichloro-5-fluorobiphenyl-2-yl)-3-difluoromethyl-1-methylpyrazole-4-carboxamide, N-(2-cyano-phenyl)-3,4-dichloroisothiazole-5-carboxamide, 2-amino-4-methyl-thiazole-5-carboxanilide, 2-chloro-N-(1,1,3-trimethyl-indan-4-yl)-nicotinamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-I H-pyrazole-4-carboxamide, N-(4'-chloro-3',5-difluoro-biphenyl-2-yl)-3-trifluoromethyl-1-methyl-1H-pyrazole-4-carboxamide, N-(3',4'-dichloro-5-fluoro-biphenyl-2-yl)-3-trifluoromethyl-1-methyl-1H-pyrazole-4-carboxamide, N-(3',5-difluoro-4'-methyl-biphenyl-2-yl)-3- difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoro-methyl-1-methyl-1H-pyrazo le-4-c arbox amide, fluopyram, N-(3-ethyl-3,5-5-trimethyl-cyclohexyl)-3-formylamino-2-hydroxy-benzamide, oxytetracyclin, silthiofam, N-(6-methoxy-pyridin-3-yl) cyclopropanecarboxamide, 2-iodo-N-phenyl-benzamide, N-(2-bicyclopropyl-2-yl-phenyl)-3-difluormethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-ylcarboxamide, N-(3',4',5'-trifluorobiphenyl-2-yl)-5-chloro-1,3-dimethyl-pyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3', 4', 5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazole-4-carboxamide, N-(3',4'-dichloro-3-fluorobiphenyl-2-yl)-1-methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-S-difluoromethyl-1H-pyrazole-4-carboxamide, N-(3'-chloro-4'-fluoro-3-fluorobiphenyl-2-yl)-1-methyl-3-difluoromethyl-1H-pyrazole-4-carboxamide, N-(3',4'-dichloro-4-fluorobiphenyl-2-yl)-1-methyl-3-trifluoromethyl-1H-pyrazole-4-carboxamide, N-(3',4'-difluoro-4-fluorobiphenyl-2-yl)-1-methyl-S-trifluoromethyl-I H-pyrazole-4-carboxamide, N-(3',4'-dichloro-4-fluorobiphenyl-2-yl)-1-methyl-3-difluoromethyl-1H-pyrazole-4-carboxamide, N-(3',4'-difluoro-4-fluorobiphenyl-2-yl)-1-methyl-3-difluoromethyl-1H-pyrazole-4-carboxamide, N-(3'-chloro-4'-fluoro-4-fluorobiphenyl-2-yl)-1-methyl-S-difluoromethyl-I H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4'-dichloro-5-fluorobiphenyl-2-yl)-1-methyl-S-difluoromethyl-I H-pyrazole-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide, N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1,3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide, N-(4'-chloro-6-fluorobiphenyl-2-yl)-1-methyl-3-trifluoromethyl-1H-pyrazole-4-carboxamide, N-[2-(1,1,2,3,3,3-hexafluoropropoxy)-phenyl]-3-difluoromethyl-1-methyl-1H-pyrazo le-4-carbox amide, N-[4'-(trifluoromethylthio)-biphenyl-2-yl]-3-difluoromethyl-1-methyl-1H-pyrazole-4-carboxamide and N-[4'-(trifluoromethylthio)-biphenyl-2-yl]-1-methyl-3-trifluoromethyl-1-methyl-1H-pyrazole-4-carboxamide; B4) heterocyclic compounds selected from the group consisting of fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methyl-piperidin-1-yl)-6-(2,4,6-trifluorophenyl)41,2,4]triazolo[1,5-alpyrimidine, anilazine, diclomezine, pyroquilon, proquinazid, tricyclazole, 2-butoxy-6-iodo-3-propylchromen-4-one, acibenzolar-S-methyl, captafol, captan, dazomet, folpet, fenoxanil, quinoxyfen, N,N-dimethyl-3-(3-bromo-6-fluoro-2-methylindole-1-sulfonyl)-[1,2,4]triazole-1-sulfonamide, 5-ethyl-6-octyl41,2,4]triazolo[1,5-a]pyrimidin-2,7-diamine, 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloro pyridin-2-yl)-methyl)-2,4-dichloro-nicotinamide, diflumetorim, nitrapyrin, dodemorphacetate, fluoroimid, blasticidin-S, chinomethionat, debacarb, difenzoquat, difenzoquat-methylsulphat, oxolinic acid and piperalin; B5) carbamates selected from the group consisting of mancozeb, maneb, metam, methasulphocarb, metiram, ferbam, propineb, thiram, zineb, ziram, diethofencarb, iprovalicarb, benthiavalicarb, propamocarb, propamocarb hydrochlorid, 4-fluorophenyl N-(1-(1-(4-cyanophenyl)-ethanesulfonyl)but-2-yl)carbamate, methyl 3-(4-chlorophenyl)-3-(2-isopropoxycarbonylamino-3-methyl-butyrylamino)propanoate; or B6) other fungicides selected from the group consisting of guanidine, dodine, dodine free base, iminoctadine, guazatine, antibiotics: kasugamycin, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts, organophosphorus compounds: edifenphos, iprobenfos, fosetyl, fosetyl-aluminum, phosphorous acid and its salts, pyrazophos, tolclofos-methyl, organochlorine compounds: dichlofluanid, flusulfamide, hexachloro-benzene, phthalide, pencycuron, quintozene, thiophanate-methyl, tolylfluanid, others: cyflufenamid, cymoxanil, dimethirimol, ethirimol, furalaxyl, metrafenone and spiroxamine, guazatine-acetate, iminoc-tadine-triacetate, iminoctadine-tris(albesilate), kasugamycin hydrochloride hydrate, dichlorophen, pentachlorophenol and its salts, N-(4-chloro-2-nitro-phenyl)-N-ethyl-4-methyl-benzenesulfonamide, dicloran, nitrothal-isopropyl, tecnazen, biphenyl, bronopol, diphenylamine, mildiomycin, oxincopper, prohexadione calcium, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethyl-silanyl-propoxy)-phenyl)-N-ethyl-N-methylformamidine and N'-(5-difluormethyl-2-methyl-4-(3-trimethylsilanyl-propoxy)-phenyl)-N-ethyl-N-methyl formamidine.

Herbicides: C1) acetyl-CoA carboxylase inhibitors (ACC), for example cyclohexenone oxime ethers, such as alloxydim, clethodim, cloproxydim, cycloxydim, sethoxydim, tralkoxydim, butroxydim, clefoxydim or tepraloxydim; phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or arylaminopropionic acids, such as flamprop-methyl or flamprop-isopropyl; C2 acetolactate synthase inhibitors (ALS), for example imidazolinones, such as imazapyr, imazaquin, imazamethabenz-methyl (imazame), imazamox, imazapic or imazethapyr; pyrimidyl ethers, such as pyrithiobac-acid, pyrithiobac-sodium, bispyribac-sodium. KIH-6127 or pyribenzoxym; sulfonamides, such as florasulam, flumetsulam or metosulam; or sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron; C3) amides, for example allidochlor (CDAA), benzoylprop-ethyl, bromobutide, chiorthiamid. diphenamid, etobenzanidibenzchlomet), fluthiamide, fosamin or monalide; C4) auxin herbicides, for example pyridinecarboxylic acids, such as clopyralid or picloram; or 2,4-D or benazolin; C5) auxin transport inhibitors, for example naptalame or diflufenzopyr; C6) carotenoid biosynthesis inhibitors, for example benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol; C7) enolpyruvylshikimate-3-phosphate synthase inhibitors (EPSPS), for example glyphosate or sulfosate; C8) glutamine synthetase inhibitors, for example bilanafos (bialaphos) or glufosinate-ammonium; C9) lipid biosynthesis inhibitors, for example anilides, such as anilofos or mefenacet; chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor; thioureas, such as butylate, cycloate, di-allate, dimepiperate, EPTC. esprocarb, molinate, pebulate, prosulfocarb, thiobencarb (benthiocarb), triallate or vemolate; or benfuresate or perfluidone; C10) mitosis inhibitors, for example carbamates, such as asulam, carbetamid, chlorpropham, orbencarb, pronamid (propyzamid), propham or tiocarbazil; dinitroanilines, such as benefin, butralin, dinitramin, ethalfluralin, fluchloralin, oryzalin, pendimethalin, prodiamine or trifluralin; pyridines, such as dithiopyr or thiazopyr; or butamifos, chlorthal-dimethyl (DCPA) or maleic hydrazide; C11) protoporphyrinogen IX oxidase inhibitors, for example diphenyl ethers, such as acifluorfen, acifluorfen-sodium, aclonifen, bifenox, chlomitrofen (CNP), ethoxyfen, fluorodifen, fluoroglycofenethyl, fomesafen, furyloxyfen, lactofen, nitrofen, nitrofluorfen or oxyfluorfen; oxadiazoles, such as oxadiargyl or oxadiazon; cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or pyrazoles, such as ET-751.JV 485 or nipyraclofen; C12) photosynthesis inhibitors, for example propanil, pyridate or pyridafol; benzothiadiazinones, such as bentazone; dinitrophenols, for example bromofenoxim, dinoseb, dinoseb-acetate, dinoterb or DNOC; dipyridylenes, such as cyperquat-chloride, difenzoquat-methylsulfate, diquat or paraquat-dichloride; ureas, such as chlorbromuron, chlorotoluron, difenoxuron, dimefuron, diuron, ethidimuron, fenuron, fluometuron, isoproturonisouron, linuron, methabenzthiazuron, methazole, metobenzuron, metoxuron, monolinuron, neburon, siduron or tebuthiuron; phenols, such as bromoxynil or ioxynil; chloridazon; triazines, such as ametryn, atrazine, cyanazine, desmein, dimethamethryn, hexazinone, prometon, prometryn, propazine, simazine, simetryn, terbumeton, terbutryn, terbutylazine or trietazine; triazinones, such as metamitron or metribuzin; uracils, such as bromacil, lenacil or terbacil; or biscarbamates, such as desmedipham or phenmedipham; C13) synergists, for example oxiranes, such as tridiphane; C14) CIS cell wall synthesis inhibitors, for example isoxaben or dichlobenil; C16) various other herbicides, for example dichloropropionic acids, such as dalapon; dihydrobenzofurans, such as ethofumesate; phenylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon; or their environmentally compatible salts.

Plant Growth Regulators: D1) Antiauxins, such as clofibric acid, 2,3,5-tri-iodobenzoic acid; D2) Auxins such as 4-CPA, 2,4-D, 2,4-DB, 2,4-DEP, dichlorprop, fenoprop, IAA, IBA, naphthaleneacetamide, a-naphthaleneacetic acids, 1-naphthol, naphthoxyacetic acids, potassium naphthenate, sodium naphthenate, 2,4,5-T; D3) cytokinins, such as 2iP, benzyladenine, 4-hydroxyphenethyl alcohol, kinetin, zeatin; D4) defoliants, such as calcium cyanamide, dimethipin, endothal, ethephon, merphos, metoxuron, pentachlorophenol, thidiazuron, tribufos; D5) ethylene inhibitors, such as aviglycine, 1-methylcyclopropene; D6) ethylene releasers, such as ACC, etacelasil, ethephon, glyoxime; D7) gametocides, such as fenridazon, maleic hydrazide; D8) gibberellins, such as gibberellins, gibberellic acid; D9) growth inhibitors, such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, tiaojiean, 2,3,5-tri-iodobenzoic acid; D10) morphactins, such as chlorfluren, chlorflurenol, dichlorflurenol, flurenol; D11) growth retardants, such as chlormequat, daminozide, flurprimidol, mefluidide, paclobutrazol, tetcyclacis, uniconazole; D12) growth stimulators, such as brassinolide, brassinolide-ethyl, DCPTA, forchlorfenuron, hymexazol, prosuler, triacontanol; D13) unclassified plant growth regulators, such as bachmedesh, benzofluor, buminafos, carvone, choline chloride, ciobutide, clofencet, cyanamide, cyclanilide, cycloheximide, cyprosulfamide, epocholeone, ethychlozate, ethylene, fuphenthiourea, furalane, heptopargil, holosulf, inabenfide, karetazan, lead arsenate, methasulfocarb, prohexadione, pydanon, sintofen, triapenthenol, trinexapac.

The presently described compositions may be in any appropriate conventional form, for example an emulsion concentrate (EC), a suspension concentrate (SC), a suspoemulsion (SE), a capsule suspension (CS), a water dispersible granule (WG), an emulsifiable granule (EG), a water in oil emulsion (EO), an oil in water emulsion (EW), a microemulsion (ME), an oil dispersion (OD), an oil miscible flowable (OF), an oil miscible liquid (OL), a soluble concentrate (SL), an ultra-low volume suspension (SU), an ultra-low volume liquid (UL), a dispersible concentrate (DC), a wettable powder (WP) or any technically feasible formulation in combination with agriculturally acceptable adjuvants. In one embodiment, the compositions can be administered directly or can be provided in a tank mix.

In another embodiment, the presently described compositions may be in the form of foamable formulations. Suitable foaming agents include, but are not limited to, nonionic surfactants, including alkanolamides (such as cocamide diethanolamide, lauric acid monoisopropanolamide, and ethoxylated myristamide), xyethylene fatty acid esters, polyoxyethylene fatty alcohol ethers (such as alkylaryl polyglycol ethers) and fluorocarbons (such as ethoxylated polyfluorinated alcohol); anionic surfactants including alkyl-, alkylaryl- and arylsulfonates (such as sodium lauryl sarcosinate and such as sodium alkylbenzenesulfonate), alkyl-, alkylaryl- and arylsulfates, protein hydrolysates, derivatives of polycarboxylic acid (such as ammonium lauryl ether carboxylate), olefin sulfonates (such as sodium alpha olefin sulfonate), sarcosinates (such as ammonium cyclohexyl palmitoyl taurinate), succinates (such as disodium N-octadecyl sulfosuccinamate), phosphorus derivatives (such as phosphoric acid esters and their equivalent salts); cationic surfactants including alkylbenzyltrimethylammonium chloride; and amphoteric surfactants including betaine. Particularly preferred foaming agents include Bio-Soft D-40, Bioterge AS-40, Ammonyx DO, Ammonyx LO, Steol CA-330, Cedepal TD-407, and Polystep B-25. The total concentration of foaming agents in the formulation will be dependent on the foaming agents used, and may comprise between about 0.1% and about 50% of the final formulation, preferably between about 0.3% and about 30%, more preferably between about 5% and 25%, and even more preferably between about 17% and about 23%.

In some embodiments, the composition is formulated as a suspension, preferably as a suspension concentrate. A suspension concentrate may contain, for example, about 50, 80, 10, 150, 200, 250, 300, 350, or 400 grams of the diamide active ingredient per liter. The concentrate can be diluted with a solvent, for example water, before being applied to a plant or soil. Tetraniliprole and its combination with one or more plant protection agents can also be prepared as a SC formulation. Various methods are known to prepare a SC formulation. An exemplary procedure is provided in U.S. Pat. No. 9,253,981, the entire disclosure of which is hereby incorporated by reference. The SC formulation may contain additional components such as a surfactant, an antifoam agent, a preservative, a thickener, water, and a suspending agent. Water is used as a diluent and preferably is purified water, for example, deionized or distilled water, and is present in an amount that would dilute the active ingredient to a desired concentration.

In some embodiments, the formulated composition is homogenous at storage condition (20-25° C.). In another embodiment, the formulated composition stays shelf stable at storage condition for at least a period of 6 years, 5 years, 4 years, 3 years, 2 years, 1 year or at least 6 months.

Preferred plant protecting agents include those that when combined with tetraniliprole, sequentially or in the same formulation would not reduce the activity of teraniliprole or compromise the stability of the formulation containing tetraaniliprole. Preferred insecticides are selected from the group consisting of abamectin, aldicarb, bendiacarb, carbaryl, carbofuran, methomyl, oxamyl, propoxur, thiodicarb, fenoxycarb, acephate, azinphos-methyl, phosmet, terbufos, endosulfan, fipronil, spinosad, milbemectin, fenoxycarb, pyriproxyfen, pymetrozine, clofentezine, etoxazole, chlorfenapyr, cartap hydrochloride, diflubenzuron, clorfluazuron, hexaflumuron, novaluron, teflubenzuron, buprofezin, cyromazine, methoxyfenozide, chromafenozide, amitraz, indoxacarb, azadirachtin and pyridaben. Preferred fungicides are selected from the group consisting of bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, pefurazoate, imazalil, triflumizole, cyazofamid, benomyl, carbendazim, thiabendazole, fuberidazole, ethaboxam, etridiazole and hymexazole, azaconazole, diniconazole-M, oxpoconazol, paclobutrazol, uniconazol, imazalilsulfphate, azoxystrobin, dimoxystrobin, fluoxastrobin, kresoxim-methyl, orysastrobin, picoxystrobin, pyraclostrobin, trifloxystrobin, enestroburin, carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, dimethomorph, flumorph, fluopicolide (picobenzamid), zoxamide, carpropamid, diclocymet, mandipropamid, bixafen, fluazinam, cyprodinil, fenarimol, ferimzone, mepanipyrim, nuarimol, pyrimethanil, fenpiclonil, fludioxonil, aldimorph, dodemorph, fenpropimorph, iprodione, procymidone, vinclozolin, famoxadone, fenamidone, probenazole, acibenzolar-S-methyl, captafol, captan, dazomet, folpet, fenoxanil, quinoxyfen, nitrapyrin, fluoroimid, blasticidin-S, chinomethionat, difenzoquat-methylsulphate, oxolinic acid, mancozeb, maneb, methasulphocarb, metiram, ferbam, propineb, thiram, zineb, ziram, diethofencarb, iprovalicarb, benthiavalicarb, propamocarb hydrochloride, guanidine, dodine, kasugamycin, validamycin A, binapacryl, dinobuton, dithianon, isoprothiolane, fosetyl-aluminum, pyrazophos, tolclofos-methyl, dichlofluanid, flusulfamide, hexachlorobenzene, phthalide, pencycuron, quintozene, thiophanate-methyl, tolylfluanid, cyflufenamid, cymoxanil, ethirimol, furalaxyl, metrafenone, iminoctadine-triacetate, iminoctadine-tris(albesilate), kasugamycin hydrochlorid-hydrat, dichlorophen, pentachlorophenol and its salts, dicloran, nitrothal-isopropyl, tecnazen, biphenyl, bronopol, diphenylamine, mildiomycin, oxine-copper and prohexadione calcium.

In some embodiments, the plant protection agent is a pyrethroid compound. Non-limiting exemplary pyrethoids include acrinathrin, allethrin, bifenthrin, bioallethrin, bioresmethrin, cyclo professional Trindade (cycloprothrin), cyfluthrin, beta-cyfluthrin, cyhalothrin, cancer better halo Trindade (gamma-cyhalothrin), lambda cyhalothrin (lambda-cyhalothrin), cypermethrin, alpha-cypermethrin, beta-cypermethrin, theta cypermethrin, zeta cypermethrin (zeta-cypermethrin), cyphenothrin, deltamethrin, empenthrin, esfenvalerate, ethofenprox, Fenpropathrin, fenvalerate, flucythrinate, flumethrin, fluvalinate, tau full burr sulfonate, halfenprox, hepta full Trindade (heptafluthrin), imiprothrin, Kadesurin, Meperufurutorin (meperfluthrin), Mon-fluoro Trindade (momfluorothrin), permethrin, phenothrin, prallethrin, pyrethrins, resmethrin, silafluofen, tefluthrin, tetramethrin, tetramethyl full Trindade, tralomethrin and Transfluthrin. In some embodiments, the plant protection agent is a pyrethroid selected from bifenthrin or zeta cypermethrin.

The plant protection agent is preferably present in a concentration of from about 1% by weight to about 55% by weight, more particularly, from about 15% by weight to about 35% by weight based upon the total weight of all components in the composition. Other exemplary ranges include from about 10% to about 35%, from about 10% to about 30%, from about 10% to about 20% by weight.

In certain embodiments where tetraniliprole is the diamide insecticide, the ratio between tetraniliprole and the plant protection agent in weight may range from about 1:100 to about 100:1, and all subranges included. In some embodiments, the ratio between tetraniliprole and the plant protection agent is in the ranges of about 1:30 to 30:1. In some embodiments, the ratio between tetraniliprole and the plant protection agent is in the ranges of about 1:15 to about 15:1. Non-limiting examples of the ratio between tetraniliprole and bifenthrin or zeta-cypermthrin include about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, and about 20:1.

In some exemplary embodiments, tetraniliprole accounts for about 1%, about 2%, about 3%, about 4%, or about 5% of the composition by weight. In some embodiments, the plant protection agent accounts for less than about 1%, about 1%, about 2%, about 3%, about 4%, about 5% of the composition by weight.

In another embodiment, the composition may include at least one additive selected from the group consisting of freeze agents, anti-foam agents and biocides. These formulation components are well-known in the agrochemical arts. In some embodiments, the anti-freeze agent is a polyalkylene glycol, preferably propylene glycol, and when present, is present in an amount from about 5% to about 9% by weight of the total of all components in the composition. In some embodiments, the anti-foam agent is an alkylcyclo-tetrasiloxane, preferably an octamethylcyclo-tetrasiloxane silicone emulsion, for example, DOW CORNING® AF Emulsion or DOWCORNING® ANTIFOAM C Emulsion (Dow Corning Corporation). If and when present in a non-foam formulation, the anti-foam agent is present in an amount of from about 0.001% to about 1% by weight of all the components in the total formulation. The preservative can be an isothiazolone or a mixture of isothiazolones, for example, KATHON® CG/ICP preservative or LEGEND® MK preservative (Rohm and Haas Corporation) or PROXEL™ BR preservative (Avecia Corporation). When present, the preservative is present in an amount of from about 0.001% to about 1% by weight of the total of all components in the formulation.

The compositions of the present invention may also contain a pH modifier. Exemplary pH ranges suitable for the present compositions include about 4-8, 4-7, 5-6, and 6-7, which includes any pH in the range of from: pH 3.5 to 3.9; 4.0 to 4.4; pH 4.5 to 5.4; pH 5.5 to pH 6.4; pH 6.5 to pH 7.4.

In another embodiment, formulations encompass a combination of the compositions according to the present invention with liquid fertilizers to be applied in one application in a single piece of equipment. One application of such a combination or formulation provides nutrients for the plant growth, while eliminating or controlling unwanted insects that can also affect the health and vitality of the desirable plants. Accordingly, the composition of the present invention may also contain a liquid fertilizer. In some embodiments, the liquid fertilizer is aqueous-based. In some embodiments, the liquid fertilizer is present in a concentration of about 95.0% by weight to about 99.99% by weight based on the total weight of all components in the composition.

According to the present invention invention carrier system is an acceptable agricultural carrier and may be a liquid, a powder, in spray or foam form to allow delivery of agriculturally effective amounts of the diamide insecticides. In at least embodiments that tetraniliprole is the diamide insecticide alone or in combination with one or more plant protection agents, the carrier system may be in the form of a suspension concentrate. Various methods are known to prepare a SC formulation. An exemplary procedure is provided in U.S. Pat. No. 9,253,981, the entire disclosure of which is hereby incorporated by reference. The SC formulation may contain additional components such as a surfactant, an antifoam agent, a preservative, a thickener, water, and a suspending agent. Water is used as a diluent and preferably is purified water, for example, deionized or distilled water, and is present in an amount that would dilute the active ingredient to a desired concentration.

Another aspect of the invention provides a method for controlling rootworms including NCR, WCRW, and SCRW at all stages of their lifecycle, egg, larva, pupa and adult form in plants and crops using the compositions of the present invention. In at least one embodiment, controlling infestation of rootworm in the corn crop can be accomplished in any soil pH. In one embodiment, the soil of the area to be protected from rootworm infestation may posses a pH in the range of from about pH 4 to about pH 9, which includes a pH in the range of from 3.5 to 9.4, or a pH of: about pH 4, about pH 5, about pH 6, about pH 7, about pH 8, or about pH 9. The method includes the step of applying to a plant or soil an effective amount of diamide insecticide including, but not limited to, flubendiamide, the phthalamide compounds (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and (S)-3-Chlor-N1-{2-methyl-441,2,2,2-tetrafluor-1-(trifluormethyl)ethyl]phenyl}-N2-(1-methyl-2-methylsulfonylethyl)phthalamid, chloranthraniliprole, cyanthraniliprole and tetraniliprole. In one embodiment, the composition may contain essentially just tetraniliprole as the sole active ingredient or may include at least one plant protection agent.

The method of the present invention can be used in pest-infested areas. However, it is also suitable for pest prevention purposes. The pests to be controlled may inhabit various places, including for example, rice paddies, fields, tea plantations, orchards, non-plant lands, houses, nursery trays or nursery boxes, nursery soil and nursery mats, and the like in the soil or at the foliage. Accordingly, the compositions can be applied in different means and forms depending on specific needs to control pests. For example, both direct spray and foliar applications can effectively control the egg production on the plant. Certainly, the method of the present invention is by no means limited to plant foliage application; other processes such as soil treatment and seed disinfection are also contemplated within the scope of the present invention. In one embodiment, the targeted pests are any WCRW and SCRW and their adult forms.

Prior to application, the concentrations of the compositions may be readjusted. For example, tetraniliprole and the plant protection agent may account for about 0.0005 to 40% by weight in the composition. Other exemplary ranges include about 0.05 to about 10%, about 0.1 to about 10%, about 0.5 to about 10%, about 1 to about 10%, and about 1 to about 5%.

In certain embodiments, tetraniliprole and the plant protection agent may be applied at a rate ranging from about 1 to 20 gallons per acre. Non-limiting examples include about 1, about 2, about 3, about 4, about 5, about 6, about 7, about 8 and about 9 gallons per acre.

As described above, tetraniliprole and the plant protection agent may be mixed together and applied in the same formulation. Alternatively, tetraniliprole and the plant protection agent can be applied sequentially. The length of the interval between the applications depends on factors such as the target pest and concentration of the ingredients and can be determined by one of ordinary skill in the art without undue experimentation.

The plants to be protected by the compositions of the present invention include, for example, agricultural crops, fruit trees and trees other than fruit trees, grass crops, and weeds. The plants can be, for example, floricultural plants, and ornamentals. Examples of agricultural crops include, but are not limited to, corn, peanut, alfalfa, rice, wheat, barley, rye, oats, sorghum, cotton, soybean, pin-nuts, buckwheat, sugar beet, rapeseed, sunflower, sugar cane, tobacco, etc., vegetables; Solanaceae vegetables (eggplant, tomato, pin-Man, peppers, potatoes, etc.), Cucurbitaceae vegetables (cucumber, pumpkin, Zucchi-two, watermelon, melon, etc.), cruciferous vegetables (radish, turnip, horseradish, co-Rurabi, Chinese cabbage, cabbage, mustard, broccoli-, cauliflower-, etc.), Asteraceae vegetables (burdock, garland *chrysanthemum*, A-Ticho-clause, lettuce, etc.), Liliaceae vegetables (leek, onion, garlic, asparagus), Umbelliferae vegetables (carrot, parsley, celery, parsnip, etc.), Chenopodiaceae vegetables (spinach, Swiss chard, etc.), Labiatae vegetables (*perilla*, mint, basil, etc.), strawberry, sweet potato, yam, taro, etc., flowers, and foliage plants. Examples of fruit trees include pome fleshy fruits (apple, pear, Japanese pear, quince, quince, etc.), stone fruit (peach, plum, nectarine, plum, cherry, apricot, pull-down, etc.), citrus (satsuma mandarin, orange, lemon, lime, gray-Pufuru-Tsu, etc.), Kenhate-rui (chestnut, walnut, hazel, A-Monde, pistachio, cashew-nuts, macadamia nuts, etc.), berries, grape, persimmon, Cage-parts, loquat, banana, co-Non-, date palm, and coconut. Examples of trees other than fruit trees include, but are not limited to, tea, mulberry, flowers and trees, street trees (ash, birch, dogwood, Yu-Cali, ginkgo, lilac, maple, oak, poplar, *Cercis chinensis*, SEAL, sycamore, *zelkova* Kurobe, fir, hemlock, juniper, pine, spruce, yew), and the like.

When and if employed with a liquid fertilizer, a hydrated aluminum-magnesium silicate may be used in the composition according to the present invention, preferably selected from montmorillonite and attapulgite. Such compositions may further include phosphate ester dispersants selected from a nonyl phenol phosphate ester and a tridecyl alcohol ethoxylated phosphate potassium salt. The dispersant or dispersants are preferably present in a total concentration of from about 0.02% by weight to about 20% by weight based upon the total weight of all components in the composition.

In one embodiment, the compositions of the present claims are superior in controlling rootworms as compared to diamide standards such as Exirel® (cyantraniliprole) and Coragen® when applied as a soil treatment against all stages and types of rootworms, particularly SCRW and WCRW larvae. In one embodiment, the tetraniliprole SC formulation of the present invention at ranges between 150 ppm to 250 ppm, preferably 200 to 225 ppm and more preferably at 213.8 ppm, provided more than 90% control to larvae and provided statistically greater control compared to all rates of Exirel (cyantraniliprole). In another embodiment, the compositions according to the present invention against WCRW, at ranges between 150 ppm to 250 ppm, preferably 200 to 225 pm and more preferably at 213.8 ppm, provide more than 92% control and statistically outperformed Exirel at similar rate and was further numerically greater than Exirel and Coragen® (chlorantraniliprole) against rootworms.

In another embodiment, the compositions of the present invention were superior in controlling rootworms when applied foliarly to infested leafs with adult beetles of *Diabrotica virgifera virgifera*. In another embodiment, compositions according to the present invention controlled rootworm larve in natural ambient condition regardless of differing water pHs 6, 7, or 8. In at least one embodiment, the composition is a tetratraniliprole SC formulation.

In another embodiment, soil treated with the formulations of the present invention containing a diamide compound provided ≥90, 95, or 98% control of $1^{st}$ and/or $2^{nd}$ instar NCR, SCRW, WCRW larvae at 64 day after treatment (DAT). In at least another embodiment, the diamide compound and bifenthrin administered in combination or sequentially provided more than ≥90, 95, or 98% control of $2^{nd}$ instar SCRW, WCRW larvae at 64 day after treatment DAT. In another embodiment, the diamide compound is tetratraniliprole.

In at least one embodiment, the present invention contains: (1) between about 1% to about 35% by weight of tetraniliprole; (2) between about about 1% to about 35% by weight of the plant protecting agent, (3) between about 1% to about 20% by weight of hydrated aluminum-magnesium silicate, and optionally (4) between about 0.2% to about 20% by weight of at least one dispersant selected from the group consisting of a sucrose ester, a lignosulfonate, an alkylpolyglycoside, a naphthalenesulfonic acid formaldehyde condensate and a phosphate ester.

In another embodiment, methods of using such formulations are described to provide ≥90, 95, or 98% control of $1^{st}$ and/or $2^{nd}$ instar NCR, SCRW, or WCRW larvae at 64 days after treatment (DAT). In at least another embodiment, the administration of tetraniliprole and bifentrin in combination or sequentially provided more than ≥90, 95, 98% control of 2$^{nd}$ instar SCRW, WCRW larvae at 64 DAT.

In another embodiment, the present invention may be in the form of a foamable formulation. Certain embodiments include stable, aqueous compositions suitable for the generation of air foams in a suitable system to provide in furrow or in situ treatment. As a result in at least one embodiment, the tetraniliprole SC formulation according to the present invention is of such consistency and flowability to generate foam when applied directly in-furrow to the seeds or if needed to form an in situ product.

The foamable formulations of the present disclosure include at least one active ingredient including traniliprole, at least one foaming agent, and at least one foam stabilizer. It is recognized that the foamable formulations may include more than one active ingredient, foaming agent and/or foam stabilizer. They may be prepared and used without dilution, or they may be diluted with water before use. The formulation may be diluted by mixing with water in the storage tank on the tractor ("tank mixing"), in these embodiments the formulation can be configured such that the mixture will remain stable upon mixing (i.e. introducing water to the formulation).

Alternatively, the formulation can be configured such that the mixture will require agitation prior to foaming, wherein the agitation can be provided by a mechanical mixture member (not shown) located within the tank. Additionally or alternatively, the mixing motion can be provided by the vibration and oscillation induced by normal operation of the tractor over the terrain. In other embodiments, mixing the formulation with water can occur within the line while it is being pumped to the foaming chamber. In an exemplary embodiment, the mixing can occur at a location upstream of the discharge or ejection nozzle(s).

In at least one embodiment, the tank mix chemical formulation has a suitable viscosity to allow the active ingredient in the foamable formulation to be delivered at a range of from 0.75-4.00 lbs a.i./gallon, and preferably from 0.75-2.00 lbs a.i./gallon. In at least one embodiment, the viscosity of the formulation is adjusted to the speed of the apparatus to provide optimal foaming at a range of speeds including approximately 4-16 ounces of chemical formulation per acre, and 24-64 ounces of water per acre and a ground speed ranging from 2-7 miles per hour. In at least one embodiment, the present invention provides the delivery of the chemical formulation with at least 0.75 lbs a.i./gallon to be delivered at a rate of at least 0.25 gallons/acre. In at least one embodiment, the tetratranilipole containing formulation is administered at a rate of about 5 to about 100 g ai/ha or about 7.5 to about 60 g ai/ha. Another aspect of the instant invention provides a foamable formulation with an expansion factor of at least 30, 40, 50, or 60.

Suitable foam stabilizers act to stabilize the foam generated from the liquid, foamable formulation. Examples of suitable foam stabilizers include, but are not limited to, glycerine, Kelzan, carrageenan, xanthan gum, guar gum, gum Arabic, gum tragacanth, polyox, alginin, and sodium alginate. Glycerine and Kelzan are particularly preferred. The total concentration of foam stabilizers in the formulation will be dependent on the foaming agents used, and may comprise between 0.1% and 15% of the total formulation, preferably 1-14%, more preferably 7-12%.

The foamable formulations of the present invention may also include dispersants, and/or preservatives. Suitable dispersants include, but are not limited to, nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulfates, alkyl- or arylsulfonates and alkyl or aryl phosphates or the corresponding PO-ether adducts, and mixtures thereox. Alkyl polyglucosides and phosphate esters are preferred dispersants.

Suitable preservatives include but are not limited to $C_{12}$ to $C_{15}$ alkyl benzoates, alkyl p-hydroxybenzoates, aloe vera extract, ascorbic acid, benzalkonium chloride, benzoic acid, benzoic acid esters of $C_9$ to $C_{15}$ alcohols, butylated hydroxytoluene, butylated hydroxyanisole, tert-butylhydroquinone, castor oil, cetyl alcohols, chlorocresol, citric acid, cocoa butter, coconut oil, diazolidinyl urea, diisopropyl adipate, dimethyl polysiloxane, DMDM hydantoin, ethanol, ethylenediaminetetraacetic acid, fatty acids, fatty alcohols, hexadecyl alcohol, hydroxybenzoate esters, iodopropynyl butylcarbamate, isononyl iso-nonanoate, jojoba oil, lanolin oil, mineral oil, oleic acid, olive oil, parabens, polyethers, polyoxypropylene butyl ether, polyoxypropylene cetyl ether, potassium sorbate, propyl gallate, silicone oils, sodium propionate, sodium benzoate, sodium bisulfite, sorbic acid, stearic fatty acid, sulfur dioxide, vitamin E, vitamin E acetate and derivatives, esters, salts and mixtures thereof. Preferred preservatives include sodium o-phenylphenate, 5-chloro-2-methyl-4-isothiazolin-3-one, 2-methyl-4-isothiazolin-3-one, and 1,2-benisothiazolin-3-one.

The compositions and methods of the present invention are further illustrated by the examples below. These examples serve only to illustrate the invention and should not be interpreted as limiting the scope of the invention in any way, since further modifications encompassed by the disclosed invention will be apparent to those skilled in the art. All such modifications are deemed to be within the scope of the invention as defined in the present specification and claims.

EXAMPLES

Figure 1:
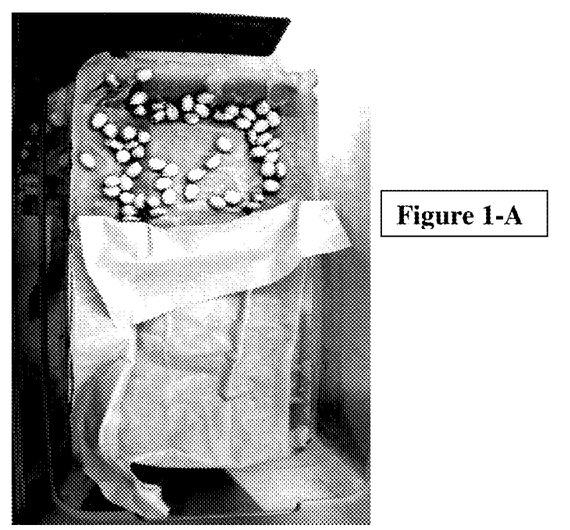

Example 1: Determination of the Insecticidal Activity of Test Formulation in Midwestern Soil In this Example, a formulation according to the present invention provided greater control to 2$^{nd}$ instar SCRW and WCRW larvae compared to the commercially available diamide standards, Exirel® (cyantraniliprole) and Coragen (chlorantraniliprole), when applied as a soil treatment.
Methodology In order to induce seed germination prior to test initiation, corn seed was submerged in water for 12 h and then placed between layers of moistened paper towel for 48 h (FIG. 1A). Plastic Dart® containers (1 oz./30 ml) were utilized for the assay (FIGS. 1C-D). Treatments included Test Formula (tetraniliprole 200 SC formulation), Rugby® (cadusafos), and chlorantraniliprole. A 60 g ai/ha foliar rate applied at a volume of 30 GPA which equates to 213.8 ppm. If this application rate was condensed into a 6" T-ban application that assumed a 30" row spacing, the ppm rate would increase to 1069 ppm (213.8 ppm×5); thus, three rates were selected for all experimental and standard treatments (213.8, 534, and 1069 ppm).

Dilutions of Test Formula (Table 1) were mixed into dry, sifted, Midwestern soil (FIG. 1B), from Wyoming, Ill., by adding 49.5 mLs of solution into 330 g of soil and equated to approximate 15% soil moisture value; soil clumped when pinched.

An estimated 0.75 cm of treated soil was placed into the bottom of each container, two germinated corn seeds were placed onto the soil, and then the arenas were capped with a lid until rootworms were infested (FIG. 1C-D). Using a fine tipped paint brush, 5 larvae ($2^{nd}$ instar) of each rootworm species (SCRW and WCRW) were transferred onto the soil of each replicate (FIG. 1E), covered with approximately 1.75 cm of treated soil, and capped (FIG. 1F).

There were 7 replicates and 35 larvae per treatment. Arenas containing soil, corn, and larvae were transferred into the Insectary room ($\approx$23° C., 0 L:24 D) and evaluated 6 days later for the presence of living SCRW and WCRW larvae. Larvae not recovered within each arena were considered dead. Longest root for each seed was recorded. All data was analyzed by ANOVA/GLM with an alpha of 0.1 (Minitab 16.0). Data points having the same letter within each column are not significantly different and were assessed using ANOVA: GLM ($\alpha$=0.1) (Table 1). The results are depicted in Table 1 below:

TABLE 1

| Treatment | Rates Tested (ppm) | Rates Tested (g ai/ha) | WRCW % Control | SCRW % Control |
|---|---|---|---|---|
| Test Formula | 213.8 | 60 | 94.3ab | 91.4a |
| Test Formula | 534 | 150 | 100a | 100a |
| Test Formula | 1,069 | 300 | 100a | 100a |
| Exirel | 213.8 | 60 | 2.96f | 8.6c |
| Exirel | 534 | 150 | 74.3 bc | 22.9c |
| Exirel | 1069 | 300 | 86.6ab | 45.7b |
| Coragen | 213.8 | 60 | 54.3cd | 11.4c |
| Coragen | 534 | 150 | 25.7ef | 8.6c |
| Coragen | 1,069 | 300 | 34.3de | 17.1c |
| Untreated | UTC | — | 11.4ef | 5.7c |

* Conversion from g ai/ha to ppm is based upon an application volume of 30 GPA (Gallones per Acre).
Note:
Values in each column that have the same letter are not statistically different when analyzed at a 90% CI, ANOVA, GLM.

As indicated in the Table 1, in a rate to rate comparison, Test Formula provided greater control to $2^{nd}$ instar SCRW and WCRW larvae compared to the diamide standards, Exirel and Coragen, when applied as a soil treatment. Coragen did not provide adequate control to rootworm larvae at any rate tested. Against SCRW, Test Formula at 213.8 ppm (91.4% a) provided statistically greater control to $2^{nd}$ instar larvae compared to all rates of Exirel. Against WCRW, Test Formula at 213.8 ppm (94.3% control) statistically outperformed Exirel at 213.8 ppm (2.9%) and was numerically greater than Exirel at 534 (74.3% bc). All surviving larvae within Test Formula treated soil (213.8 ppm) were controlled, stunted, had not grown, and differed from all other surviving larvae within other treatments and rates.

Conclusion

In conclusion, against SCRW, Test Formula at 213.8 ppm provided some 91.4% control to larvae and provided statistically greater control compared to all rates of cyantraniliprole. Against WCRW, Test Formula at 213.8 ppm provided 94.3% control, and statistically outperformed cyantraniliprole. In fact, Test Formula of the present invention outperformed cyantraniliprole at 535 ppm.

Example 2

In this example, Test Formula was compared with Belt®, Coragen®, and Exirel® in both direct spray and foliar applications against SCRW and WCRW. The results indicated that the Test Formula provided greater control to SCRW and WCRW adults (direct contact and feeding). In addition, against SCRW and WCRW adults, Test Formula was more effective than Belt, Coragen, and Exirel in both direct spray and foliar applications against Southern and Western corn rootworm adults (SCRW+WCRW).

Methodology

Direct Spray: Three replicates of five adult beetles (n=15) were placed into 12 oz. Styrofoam containers on the day of application. Both southern and western corn rootworms (SCRW and WCRW) were evaluated in the bioassay. Treatments and rates are listed in Table 1 and were applied using a DeVilbiss sprayer in accordance with SOP 529.00 with the deviation of beetles being sprayed at 40 p.s.i. Beetles were immediately transferred to clean containers and provisioned with a water source and a clipped cucumber leaf. At 2 Days After Administration (DAA), mortality and % feeding damage were assessed. Because leaves varied in size, a single untreated check leaf was used as a reference to compare to all other replicates. After the initial assessment of feeding damage, the leaf was discarded and a freshly cut, untreated cucumber leaf was placed back into each arena. At 4 DAA, mortality was recorded.

Foliar Spray: Four leaf staged cucumber plants were trimmed down to the two youngest leaves, the upper and lower leaves sprayed with the DeVilbiss at 40 p.s.i., and placed in the drying hood until dry. A single leaf was cut and placed over the water source within a 12 oz. Styrofoam container. Scissors were cleaned with 70% EtOH between treatments. Three replicates of five adult beetles (n=15) were infested onto the leaf of each container. Both southern and western corn rootworms (SCRW and WCRW) were evaluated in the bioassay. Assessment timing and methods were synonymous to the direct spray component of the assay.

The results of the direct spray applications are depicted in Table 2 below:

TABLE 2

| | | DIRECT SPRAY | | | | | |
|---|---|---|---|---|---|---|---|
| | | Avg % Control to SCRW | | Avg % Control to WCRW | | % Feeding Damage at 2DAA | |
| Treatment | Rate (g ai/ha) | 2DAA | 4DAA | 2DAA | 4DAA | SCRW | WCRW |
| Exirel | 7.5 | 13.3c | 13.3b | 13.3c | 40.0bcde | 27.7abcd | 21.7cd |
| | 15 | 6.7c | 6.7b | 0.0c | 13.3de | 9.0cde | 7.7de |
| | 30 | 0.0c | 8.3b | 13.3c | 20.0cde | 10.7bcde | 7.3de |
| | 60 | 6.7c | 20.0b | 0.0c | 26.7cde | 3.3de | 2.0e |
| Coragen | 7.5 | 0.0c | 0.0b | 6.7c | 6.7e | 36.7a | 40.0abc |
| | 15 | 13.3c | 13.3b | 0.0c | 8.3de | 35.0ab | 26.7bc |
| | 30 | 0.0c | 6.7b | 0.0c | 13.3de | 38.3a | 31.7abc |
| | 60 | 0.0c | 0.0b | 0.0c | 13.3de | 31.7abc | 36.7abc |

TABLE 2-continued

| | | DIRECT SPRAY | | | | | |
|---|---|---|---|---|---|---|---|
| | | Avg % Control to SCRW | | Avg % Control to WCRW | | % Feeding Damage at 2DAA | |
| Treatment | Rate (g ai/ha) | 2DAA | 4DAA | 2DAA | 4DAA | SCRW | WCRW |
| Belt | 7.5 | 6.7c | 6.7b | 0.0c | 6.7e | 36.7a | 45.0ab |
| | 15 | 8.3c | 8.3b | 30.0bc | 48.3bcde | 36.7a | 30.0abc |
| | 30 | 0.0c | 0.0b | 6.7c | 6.7e | 41.7a | 46.7a |
| | 60 | 0.0c | 0.0b | 0.0c | 20.0cde | 40.0a | 38.3abc |
| Brigade | 11 | 100.0a | 100.0a | 100.0a | 78.3ab | 0.0e | 0.0e |
| | 22 | 100.0a | 100.0a | 100.0a | 100.0a | 0.0e | 0.0e |
| | 44 | 100.0a | 100.0a | 100.0a | 100.0a | 0.0e | 0.0e |
| | 88 | 100.0a | 100.0a | 100.0a | 100.0a | 0.0e | 0.0e |
| Test Formula | 7.5 | 13.3c | 86.7a | 13.3c | 46.7bcd | 0.0e | 1.3e |
| | 15 | 48.3b | 93.3a | 0.0c | 56.7bc | 1.7e | 1.3e |
| | 30 | 65.0b | 93.3a | 26.7bc | 40.0bcde | 0.3e | 1.3e |
| | 60 | 65.0b | 100.0a | 58.3b | 71.7ab | 0.3e | 0.0e |
| UTC | — | 0.0c | 0.0b | 13.3c | 20.0cde | 50.0a | 33.3abc |

Note:
Statistical analysis (GLM/ANOVA; CI = 90%) compared differences within each individual column The results of the foliar spray applications are depicted in Table 3 below:

TABLE 3

| | | Foliar | | | | | |
|---|---|---|---|---|---|---|---|
| | | Avg % Control to SCRW | | Avg % Control to WCRW | | % Feeding Damage at 2DAA | |
| Treatment | Rate (g ai/ha) | 2DAA | 4DAA | 2DAA | 4DAA | SCRW | WCRW |
| Exirel | 7.5 | 6.7c | 6.7c | 6.7d | 20.0bc | 9.3cde | 10.0efg |
| | 15 | 0.0c | 0.0c | 20.0cd | 33.3bc | 7.3de | 8.0efg |
| | 30 | 0.0c | 0.0c | 0.0d | 13.3c | 5.3de | 8.3efg |
| | 60 | 5.6c | 6.7c | 6.7d | 25.6bc | 3.7e | 6.3efg |
| Coragen | 7.5 | 5.6c | 5.6c | 6.7d | 13.3c | 16.7cde | 31.7abc |
| | 15 | 0.0c | 8.3c | 0.0d | 20.6bc | 25.0bcd | 21.7cde |
| | 30 | 0.0c | 0.0c | 20.0cd | 46.7bc | 11.0cde | 13.0defg |
| | 60 | 0.0c | 0.0c | 20.0cd | 26.7bc | 16.7cde | 20.0cdef |
| Belt | 7.5 | 0.0c | 0.0c | 0.0d | 24.4bc | 28.3abc | 46.7a |
| | 15 | 0.0c | 0.0c | 6.7d | 13.3c | 41.7ab | 31.7abc |
| | 30 | 0.0c | 6.7c | 0.0d | 13.3c | 40.0ab | 40.0ab |
| | 60 | 0.0c | 0.0c | 20.0cd | 46.7bc | 38.3ab | 28.3bcd |
| Brigade | 11 | 100.0a | 94.4ab | 100.0a | 60.0ab | 0.0e | 0.0g |
| | 22 | 100.0a | 100.0a | 100.0a | 100.0a | 0.0e | 0.0g |
| | 44 | 100.0a | 100.0a | 100.0a | 100.0a | 0.0e | 0.0g |
| | 88 | 100.0a | 100.0a | 100.0a | 100.0a | 0.0e | 0.0g |
| Test Formula | 7.5 | 13.3c | 26.7c | 13.3d | 26.7bc | 2.7e | 5.0fg |
| | 15 | 0.0c | 20.0c | 40.0bc | 53.3bc | 3.3e | 1.3g |
| | 30 | 53.3b | 41.7c | 40.0bc | 53.3bc | 1.3e | 2.0g |
| | 60 | 0.0c | 47.6bc | 53.3b | 46.7bc | 1.7e | 2.0g |
| UTC | — | 0.0c | 0.0c | 6.7d | 20.0bc | 46.7a | 38.3ab |

Note:
Statistical analysis (GLM/ANOVA; CI = 90%) compared differences within each individual column Conclusion Direct Spray:

SCRW: Against Southern corn rootworms, all rates of Test Formula (7.5 g to 60 g ai/ha) were statistically equivalent to Brigade and provided a greater level of control (86.7% to 100%) compared to the diamide standard products Exirel (8% to 20%), Coragen (0% to 13%), and Belt (0% to 8.3%) when applied directly to beetles. At 2 DAA, no feeding on untreated leaves was observed on SCRW sprayed with all rates of Brigade. Feeding damage by SCRW beetles treated with Test Formula ranged between 0.0% to 1.7%, was statistically lower than Coragen and Belt, and numerically reduced compared to Exirel.

WCRW: Western corn rootworms were less susceptible to direct applications of all treatments compared to SCRW; at 60 g ai/ha, Test Formula provided greater control (72%) compared to the diamide standards, Exirel, Coragen, Belt. Feeding damage by WCRW beetles was similar to the SCRW data; beetles treated with Test Formula had feeding damage ranging between 0.0% and 1.3%, was statistically lower than Coragen and Belt, and numerically reduced compared to Exirel.

Foliar Spray:

SCRW: At 60 g ai/ha, Test Formula provided 48% control when sprayed to the foliage of cucumber plants compared to Exirel 7%, Coragen, 0%, and Belt, 0%. When Brigade treatments were removed from the statistical evaluation within Minitab, Test Formula provided statistically improved control compared to the standard diamides. Leaves treated with Test Formula had damage ranging between 1.3% and 3.3%, which was statistically lower than Belt, and numerically reduced compared to Coragen and Exirel. The amount of feeding damage was similar to the direct spray beetle component of the assay. Treated leaves were removed at 2 DAA and replaced with untreated leaves; mortality would have likely continued to increase if the beetles remained on treated foliage.

WCRW: Similar mortality was observed between WCRW and SCRW infested upon Test Formula treated foliage. Accordingly the Test Formula provided 47% control vs. Exirel (27%), Coragen (27%), Belt (47%). The untreated check WCRW adults had 20% mortality at 4 DAA, had the same mortality as the direct spray WCRW untreated checks, but were different cohorts. Brigade at the lowest tested rate (11 g ai/ha) had 40% recovery between 2 DAA and 4 DAA (60% mortality). Untreated check mortality, coupled with the low number of beetles per treatment (N=15), likely prevented statistical separation between treatments.

In conclusion, in both direct spray and foliar applications Test Formula provided statistically improved control compared to the standard product Belt and numerical and/or statically greater control compared to Coragen and Exirel.

Example 3

In this example, the activity of Test Formula treatment applied to Midwestern soil had extended residual activity against *Diabrotica virgifera virgifera*.

Methodology

Dilutions of Test Formula were mixed into dry, sifted, Midwestern soil (FIG. 1B), from Wyoming, Ill., by adding 300 ml of solution into 2000 g of soil and equated to approximate 15% soil moisture value; soil clumped when pinched. Treated soil was maintained in 3" pots (8 pots per treatment) within greenhouse. Pots were watered from above one time per day to maintain soil at approximately 15% moisture.

An estimated 0.75 cm of treated soil was placed into the bottom of each container, two germinated corn seeds were placed onto the soil, and then the arenas were capped with a lid until rootworms were infested (FIG. 1C-D). Using a fine tipped paint brush, 5 larvae ($2^{nd}$ instar) of each rootworm species (SCRW and WCRW) were transferred onto the soil of each replicate (FIG. 1E), covered with approximately 1.75 cm of treated soil, and capped (FIG. 1F).

There were 8 replicates and 40 larvae per treatment. Arenas containing soil, corn, and larvae were transferred into the Insectary room (≈23° C., 0 L:24 D) and evaluated 6 days later for the presence of living SCRW and WCRW larvae. Larvae not recovered within each arena were considered dead. All data was analyzed by ANOVA/GLM with an alpha of 0.1 (Minitab 16.0). Data points having the same letter within each column are not significantly different and were assessed using ANOVA: GLM (α=0.1). The results are depicted in Table 4 below:

TABLE 4

| Treatment | Rates Tested (ppm) | In-furrow Application Rate* (g ai/ha) | 2nd instar WCRW: % Mortality | | |
|---|---|---|---|---|---|
| | | | 14DAT | 28DAT | 43DAT |
| Test Formula | 66.8 | 3.75 | 92.5 a | 97.5 a | 82.5 b |
| Test Formula | 133.6 | 7.5 | 97.5 a | 100 a | 90 ab |
| Test Formula | 267.3 | 15 | 100 a | 100 a | 100 a |
| Test Formula | 534.5 | 30 | 100 a | 100 a | 97.5 a |
| Test Formula | 1069 | 60 | 100 a | 100 a | 97.5 a |

TABLE 4-continued

| Treatment | Rates Tested (ppm) | In-furrow Application Rate* (g ai/ha) | 2nd instar WCRW: % Mortality | | |
|---|---|---|---|---|---|
| | | | 14DAT | 28DAT | 43DAT |
| Capture LFR | 3,977 | 223.2 | 100 a | 100 a | 100 a |
| Rugby | 1,069 | 60 | 100 a | 100 a | 100 a |
| Untreated | UTC | | 10 b | 2.5 b | 2.5 c |

*rates calculated based upon a 6" T-ban with a 30" row spacing same letters within a column are not significantly different (ANOVA, CI 90%)

Conclusion

Test Formula applied to soil maintained in fluctuating ambient conditions within the greenhouse at rates of ≥15 g ai/ha provided 97.5 to 100% control out to 43 DAT. The efficacy provided by the 2 lower rates of Test Formula were beginning to diminish at this time point. The lowest rate tested (3.75 g ai/ha) provided statistically reduced control (83% b) at 43 DAT. This break in treatment efficacy suggests that the product will ultimately break down in soil within a field setting.

Example 4

Soil treated with a formulation according to the present invention and maintained outdoors was evaluated for activity for WCRW larvae.

The efficacy of the formulation of the present invention on control of rootworm larve was evaluated after it was applied to soil and maintained in natural ambient condition and was subjected to differing water pHs (6, 7, and 8) applied daily to soil.

Methodology

A solution of the Test Formula A was prepared by making dilutions in water to form a solution. Dry, Midwestern soil was brought up to 15% moisture with treatment solutions (Table 5). Buckets of treated soil were carted outside daily between Monday and Friday and exposed to direct sunlight. Carts were not wheeled out on days that forecasted precipitation. At the end of each day, soil buckets were brought back into the laboratory, weighed, the appropriate amount of water added to the soil to bring it back up to 15% moisture, and covered overnight; daily records of weights and amount of water added to each bucket was recorded. The deionized water ($dH_2O$) had a pH of approximately 5.0 and was altered with 0.5M KOH to a final pH of 6, 7, and 8.

At 30 DAT, 42 DAT, 57 DAT, and 85 DAT, $2^{nd}$ instar WCRW larvae were infested into treated soil containing and germinating corn seed and evaluated 6 days after infestation (6 DAI) for percent control and larval stunting. There were 6 replicates per infestation date with 5 larvae per replicate (n=30). Treatments applied to dry Midwestern soil for assessment of residual WCRW included Test Formula at 67, 267, and 1,069 ppm, Capture LFR at 1988.5 and 3,977 ppm.

Table 5 below provides the mortality rates of $2^{nd}$ instar WCRW larvae infested into treated soil exposed to direct sunlight at 85 days after treatment.

| Treatment | Rate (ppm) | pH | No Dead per replicate (n = 5) at 85 DAT | | | | | | Avg % Mortality |
|---|---|---|---|---|---|---|---|---|---|
| | | | 1 | 2 | 3 | 4 | 5 | 6 | |
| Test Formula | 67 | 6 | 5 | 5 | 5 | 4 | 5 | 5 | 96.67 a |
| Test Formula | 67 | 7 | 4 | 5 | 4 | 4 | 5 | 4 | 86.67 a |
| Test Formula | 67 | 8 | 3 | 4 | 5 | 5 | 4 | 5 | 86.67 a |

-continued

| Treatment | Rate (ppm) | pH | No Dead per replicate (n = 5) at 85 DAT | | | | | | Avg % Mortality |
|---|---|---|---|---|---|---|---|---|---|
| | | | 1 | 2 | 3 | 4 | 5 | 6 | |
| Capture LFR | 1988.5 | 7 | 5 | 5 | 5 | 5 | 5 | 5 | 100.0 a |
| Untreated Check | — | 7 | 1 | 0 | 0 | 1 | 2 | 0 | 13.33 b |

Note:
same letters within a column are not significantly different when analyzed via ANOVA: GLM ($\alpha = 0.1$)

Figure 2:
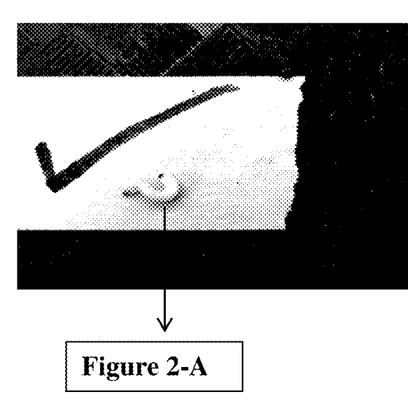

All three rates of tetraniliprole Test Formula as shown in Table 5 above, provided 100% control up to 42 DAT. The lowest rate of tetraniliprole (67 ppm) was further assessed at 57 DAT and 85 DAT. No statistical difference in the level of WCRW control was detected between tetraniliprole treated soil kept at 15% moisture using pH (6, 7, or 8) altered, deionized water (Table 5). At 57 DAT and 85 DAT, all surviving larvae recovered from Test Formula treated soil were severely stunted compared to the non-treated check (FIG. 2). At 85 DAT, Test Formula treated soil that had moisture maintained with water at a pH of 6 provided 97% control but was not significantly different from pH 7 or pH 8.

Conclusion

A solution containing tetraniliprole at 67 ppm (3.75 g ai/ha) was incorporated into Midwestern soil (15% moisture) and maintained outdoors provided control to WCRW larvae. This amount of tetraniliprole was equivalent to Capture LFR ($\alpha$=0.1). Soil of each treatment was manipulated daily with water at pH 6, 7, or 8. A tetraniliprole containing formulation according to the present invention provided ≥87% control with all surviving larvae being severely stunted compared to the non-treated check Example 5: Efficacy of Test Formula Treated Soil Against WCRW Larvae In this example residual activity and stability of tetraniliprole test treatments within microbially active Midwestern soil against $2^{nd}$ nymphal stage WCRW-*Diabrotica virgifera virgifera* was assessed in corn field and further compared to Capture LFR and Rugby.

Methodology

In order to induce seed germination prior to test initiation, corn seed was submerged in water for 12 h and then placed between layers of moistened paper towel for 72 h. Plastic Dart® containers (1 oz/30 ml) were utilized for the assay. Treatments included tetraniliprole Test Formula according to the present invention, Capture LFR® (bifenthrin), and Rugby® (cadusafos). A 60 g ai/ha foliar rate applied at a volume of 30 GPA equates to 213.8 ppm. If this application rate was condensed into a 6" T-band application that assumed a 30" row spacing, the ppm rate would increase to 1069 ppm (213.8 ppm×5). Five rates were selected for the experimental treatment (Test Formula) and compared to a single rate of two standard treatments (Capture LFR and Rugby). Treatment solutions (Table 4) were mixed into dry, sifted, Midwestern soil, from Wyoming, Ill., by adding 300 mLs of solution into 2000 g of soil and equates to approximate 15% soil moisture value; soil clumped when pinched.

An estimated 0.75 cm of treated soil was placed into the bottom of each container, one germinated corn seed was placed onto the soil, and then the arenas were capped with a lid until rootworms were infested. Corn was covered with approximately 1.75 cm of treated soil. Using a fine tipped paint brush, 5 WCRW larvae ($2^{nd}$ instar) were transferred onto the soil of each replicate and then capped. There were 8 replicates and 40 larvae per treatment. Arenas containing soil, corn, and larvae were transferred into the Insectary room ($\approx$23° C., 0 L:24 D) and evaluated 6 days later for the presence of living larvae. Larvae not recovered within each arena were considered dead. Additional treated soil was maintained within a 5 gallon bucket, covered with aluminum soil, and weights recorded. Additional water was added every Monday in order to maintain a 15% soil moisture level.

All mortality data was analyzed by ANOVA/GLM with an alpha of 0.1 (Minitab 16.0). Data points having the same letter within each column are not significantly different and were assessed using the Tukey Method (Table 5).

Figure 3:
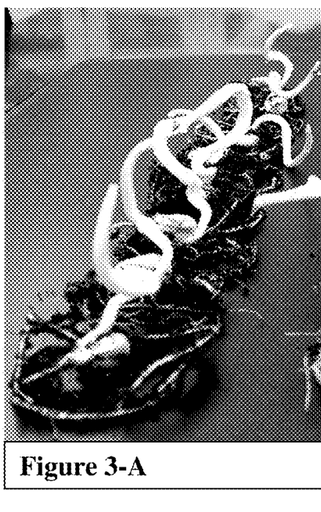
Figure 4:
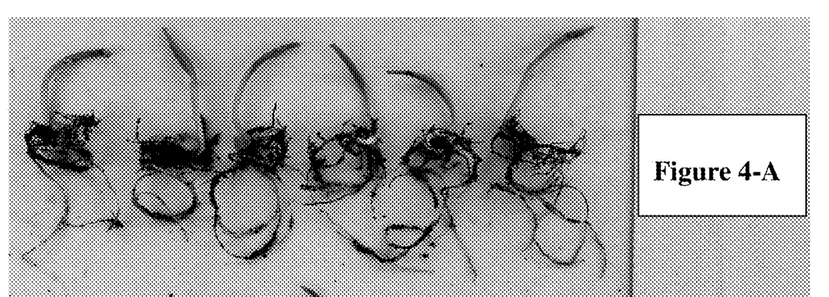

At 0 DAT: tetraniliprole treated soil at 30 and 60 g ai/ha provided 97.5% control to $2^{nd}$ instar WCRW. This bioassay confirms the activity of tetraniliprole against rootworms as shown in Example 1. Stunted larvae were detected in all tetraniliprole treated soils compared to the untreated check. At the lowest rate tested (3.75 g aiha), larvae were approximately half the size as the untreated check; a single, drastically stunted larvae were found at the two highest rates tested. Protection to the root and shoot system of corn was evident with all tetraniliprole treated soils (FIG. 3). The lowest two rates of tetraniliprole (3.75 g and 7.5 g ai/ha) were not infested at 14 DAT due to rates providing <80% control at 0 DAT.

At 14 DAT: The 15 g ai/ha rate of tetraniliprole formulation according to the present invention provided greater control at 14 DAT compared to 0 DAT. Those of ordinary skill in the art would understand that the lower rates (3.75 and 7.5 g ai/ha) at residual evaluation dates would be as effective in future assays.

At 28, 50, and 64 DAT: All soil treatments remaining in the bioassay provided ≥95% control out to 64 DAT (Table 6).

TABLE 6

Mortality of $2^{nd}$ instar WCRW after 144 h within treated soil.

| Treatment | Rates Tested (ppm) | In-furrow Application Rate* (g ai/ha) | 2nd instar WCRW: % Mortality | | | | |
|---|---|---|---|---|---|---|---|
| | | | 0 DAT | 14 DAT | 28 DAT | 50 DAT | 64 DAT |
| Test Formula | 66.8 | 3.75 | 57.5 c | — | — | — | — |
| Test Formula | 133.6 | 7.5 | 77.5 bc | — | — | — | — |
| Test Formula | 267.3 | 15 | 87.5 ab | 95.0 a | 100.0 a | 100.0 a | 95.0 a |
| Test Formula | 534.5 | 30 | 97.5 ab | 100.0 a | 100.0 a | 100.0 a | 95.0 a |
| Test Formula | 1069 | 60 | 97.5 ab | 100.0 a | 100.0 a | 100.0 a | 100.0 a |

TABLE 6-continued

Mortality of 2$^{nd}$ instar WCRW after 144 h within treated soil.

| Treatment | Rates Tested (ppm) | In-furrow Application Rate* (g ai/ha) | 2nd instar WCRW: % Mortality | | | | |
|---|---|---|---|---|---|---|---|
| | | | 0 DAT | 14 DAT | 28 DAT | 50 DAT | 64 DAT |
| Capture LFR | 3,977 | 223.2 | 100.0 a | 100.0 a | 100.0 a | 100.0 a | 100.0 a |
| Rugby | 1,069 | 60 | 100.0 a | 100.0 a | 100.0 a | 100.0 a | 100.0 a |
| Untreated | UTC | | 2.5 d | 0.0 b | 7.5 b | 0 b | 17.5 b |

*rates calculated based upon a 6" T-ban with a 30" row spacing
—treated soil not infested after 0 DAT
Note:
rows having the same letter are not significanly different when analyzed via ANOVA: GLM (a = 0.1)

Conclusion

Tetraniliprole treated Midwestern soil (15, 30, 60 g ai/ha) maintained in the lab at a 15% moisture level provides ≥95% control to 2$^{nd}$ instar WCRW larvae at 64 DAT. Both Capture LFR® (bifenthrin) and Rugby® (cadusafos) provided 100% mortality.

While this invention has been described with an emphasis upon preferred embodiments, it will be obvious to those of ordinary skill in the art that variations in the preferred compositions and methods can be used and that it is intended that the invention can be practiced otherwise than as specifically described herein. Accordingly, this invention includes all modifications encompassed within the spirit and scope of the invention as defined by the claims that follow.

The invention claimed is:

1. A liquid agricultural formulation consisting essentially of (a) a sole active insecticidal component selected from the group consisting of tetraniliprole present in an amount of from 1 to 35% by weight of the formulation, and (b) a carrier system, wherein the agricultural formulation is in the form of a microemulsion, an oil-in-water concentrated emulsion, a suspension, a suspension concentrate, an emulsifiable concentrate, or a microencapsulate and is effective in inducing mortality in at least 60% of *Diabrotica* rootworm larvae and wherein said formulation excludes chlorantraniliprole.

2. The formulation of claim 1, wherein the carrier system comprises at least one foaming agent and at least one foam stabilizer.

3. The formulation of claim 1, wherein the formulation is in the form of a suspension concentrate.

4. The formulation of claim 3, wherein the tetraniliprole is present in an amount of from 1 to 5 wt % of the formulation composition.

5. A liquid agricultural formulation consisting essentially of (a) tetraniliprole present in an amount of from 1 to 35% by weight of the formulation, (b) a carrier system, wherein the agricultural formulation is in the form of a microemulsion, an oil-in-water concentrated emulsion, a suspension, a suspension concentrate, an emulsifiable concentrate, or a microencapsulate and is effective in inducing mortality in at least 60% of *Diabrotica* rootworm larvae and wherein said formulation excludes chlorantraniliprole, and further comprising (c) a plant protecting agent selected from the group consisting of insecticides, pesticides, fungicides, herbicides, fertilizers and combinations thereof.

6. The formulation of claim 5, wherein the plant protecting agent is a pyrethroid insecticide selected from the group consisting of: acrinathrin; allethrin; bifenthrin; cyfluthrin; cypermethrin; alpha-cypermethrin; beta-cypermethrin; zeta-cypermethrin; deltamethrin; esfenvalerate; etofenprox; fenpropathrin; fenvalerate; flucythrinate; tau-fluvalinate; permethrin; silafluofen; gamma-cyhalothrin; and tralomethrin.

7. The formulation of claim 6, wherein the plant protecting agent is bifenthrin.

* * * * *